United States Patent [19]

Bonfanti

[11] Patent Number: 4,912,211

[45] Date of Patent: Mar. 27, 1990

[54] METHOD FOR PRODUCING PURE CRYSTALLINE ANTIBIOTIC PRODUCTS

[76] Inventor: Giovanni Bonfanti, Parco Diana 04023, S. Croce Formia Lt, Italy

[21] Appl. No.: 118,888

[22] Filed: Nov. 10, 1987

[30] Foreign Application Priority Data

Dec. 23, 1986 [IT] Italy ................ 22852 A/86

[51] Int. Cl.$^4$ .................. C07D 501/12; C07D 499/18
[52] U.S. Cl. ..................... 540/222; 540/227; 540/228; 540/230; 540/221; 540/314; 540/327
[58] Field of Search ............... 540/227, 222, 228, 226, 540/230, 327, 314

[56] References Cited

PUBLICATIONS

The Merck Index (Tenth Edition), p. 276.
A Textbook of Practical Organic Chemistry, pp. 122–125 (1956), John Wiley & Sons, Inc.
Merck Index, pp. 1018, 1019, 268–272 (Tenth Edition) 1983.

Primary Examiner—Nicholas S. Rizzo
Attorney, Agent, or Firm—Oblon, Spivak, McClelland, Maier & Neustadt

[57] ABSTRACT

A process is described for producing pure crystalline products, in particular penicillin and cephalosporin, wherein the desired product, prepared according to a known method, is treated with ethanol in one or two steps, whereby the crystallization of the pure product and impurity separation are achieved.

1 Claim, No Drawings

METHOD FOR PRODUCING PURE CRYSTALLINE ANTIBIOTIC PRODUCTS

DESCRIPTION

The present invention relates to a new method for obtaining pure crystalline products, free from toxic solvents, to be used in the pharmaceutical field.

Object of the present invention are also the products, obtained using the process according to the invention, showing physico-chemical properties different from the known products.

The method is based on the principle that products, which are obtained as amorphous material or in a crystalline form different from, and less stable than a stable crystalline form, are transformed when in suspension or in solution in another solvent, wherein they can possibly crystallize as a more stable form.

Such a principle is a general one and can be applied in almost all the fields.

A particular object of the invention is a method for producing such penicillins or cephalosporins, which can be crystallized from solvents as pure substances containing ethanol as only residual solvent.

According to the method of the invention, the desired final product can be obtained and dried using known techniques and then transformed into the finished desired product by suspending it in anhydrous or hydrous ethanol. Some products are preferably dissolved in variously hydrated ethanol and then crystallized by dilution with absolute ethanol.

The operative temperature is in general different for the various products, because, in all the cases, the optimum temperature has to be selected for both the dissolution and the crystallization, the crystallized solution being preferably cooled.

In order to obtain pure products free from toxic solvents, according to the invention, an amorphous product can be transformed into the corresponding crystalline product by dissolving and crystallizing it in anhydrous or hydrous ethanol.

Such an amorphous product can be obtained by freeze-drying, concentration under high vacuum, spray-drying or other means, usually known in the art.

The thus resulting products can be afterwards easily crystallized from ethanol in order to obtain, at the same time, the desired crystalline form and the removal of the impurities formed in the previous steps.

The process according to the invention allows said products to be obtained with high yields and the use of foreign substances, such as sodium ethylhexanoate, commonly employed in the precipitation of such antibiotics, to be avoided, the presence of these substances in the finished products being at the same time prevented.

More particularly, the product obtained according to known techniques is extracted by a water-immiscible solvent, fit for extracting the product in acid form from water. In this step are eliminated all the water-soluble inorganic salts and degradation products.

The product is afterwards re-extracted by pure, distilled water and transformed into the sodium salt by adding sodium hydroxide, carbonate or bicarbonate.

The aqueous phase, now containing in general only the product in form of sodium salt with traces of impurities, if any, is then dried according to one of the above-mentioned methods (freeze-drying, concentration under high vacuum, spray-drying) so as to obtain an amorphous, but stable powder.

The resulting powder is treated, preferably in two steps, with ethanol, wherein the product dissolves and then the finished product crystallized.

Before the beginning of the crystallization, the solution can be filtered in order to eliminate the foreign, insoluble substances, if any, present in the solvent.

During the crystallization process, the purification of the products results because the impurities, possibly present, do not crystallize.

In the following some examples are given, which are illustrative of the employed techniques, but non limitative as far as the variety of the obtainable products is concerned.

EXAMPLE 1

50 g of 6-aminopenicillanic acid (6-APA) are dissolved in 500 ml of water with a 10% solution of sodium hydroxide.

To the clear solution 300 ml of acetone and 20 g of sodium bicarbonate are added. Then a solution of 60 g of 6-chlorophenyl-5-methyl-4-isoxazolyl chloride in anhydrous acetone is added and the mixture is stirred over a 1,5 h period up to reaction completed. Acetone is then extracted from water by adding 1000 ml of methylene chloride. After phase separation, the organic phase is discarded and to the aqueous phase 1000 ml of methylene chloride are added. The pH is slowly adjusted to 2,5 with 10% sulphuric acid. In this step cloxacillin goes into the solvent and the water-soluble inorganic salts and degradation products remain in the aqueous phase. 300 ml of distilled water are added to the organic phase, the pH is adjusted to 7 with sodium hydroxide solution, the phases are separated and the aqueous phase, previously filtered on coal, is freeze-dried. 106 g of product are obtained, having an activity of 96% and a moisture content of less than 1%. The powder so obtained is dissolved in 400 ml of absolute ethanol, the resulting solution is filtered and the filter washed with 50 ml of ethanol. 10 ml of deionized water are added.

The mixture is heated to 30° C. over a 1 h period, then cooled to 10° C. and the crystallization continued during 3 h. The mixture is filtered, the filter-cake washed with 100 ml of absolute ethanol and dried under vacuum at 50° C., whereby 104 g of sodium cloxacillin monohydrate containing 3,2% moisture are obtained; purity; wet product 96,2%, dry product 99,4%. The residual solvent is 0,15% concentrated ethanol, by gas-chromatography.

EXAMPLE 2

50 g of 6-APA are dissolved in 500 ml of water with a 10% solution of sodium hydrodide. 300 ml of acetone and then, in the course of 10 minutes, 74 g of 2,6-dichlorophenyl-5-methyl-4-isoxazolyl chloride in 500 ml of acetone are added. The mixture is reacted over a 1,5 h period, while controlling pH which drops to 2,1. 500 ml of methylene chloride are added, the mixture is stirred for 5 minutes an then the phases are separated. The organic phase is washed twice with 500 ml of water in order to remove acetone, then 1000 ml of distilled water are added and pH adjusted to 7 with sodium hydroxide solution. The phases are separated and the aqueous phase is filtered on coal for eliminating the colour and concentrated under vacuum to dryness, the miner temperature being not over 25° C. The dry product is put in 500 ml of absolute ethanol. The mixture is stirred over a period of 4 h until the raw material, resulting from the first step, is totally transformed into a white, crystalline product.

The product so obtained is filtered, washed with 100 ml of absolute ethanol and dried under vacuum at 50° C. until the solvent is completely removed.

108 g of sodium dicloxacillin monohydrate are obtained containing 3,5% water and less than 0,1% solvent; purity: wet product 96%, dry product 99,9%.

EXAMPLE 3

100 of sodium flucloxacillin containing about 1,4% of ethyl acetate, purity 97,2% (dry product), are dissolved in 400 ml of distilled water. The product is ten Spray-dried until a white, amorphous powder with a moisture content of less than 2% is obtained.

This product is suspended in 300 m of 95% ethanol. The crystallization is carried out under slow stirring while cooling at 0° C. The product is filtered, washed with 100 l of 95% ethanol and dried under vacuum. 96 g of crystalline product are obtained having a moisture content of 3,5 %; purity: wet product 96,2%, dry product 99,7%. The residual solvent comprises only ethanol in amount less than 0,1%.

EXAMPLE 4

100 g of flucloxacillin obtained according to usual methods are slowly added to 400 ml of absolute ethanol.

During the addition the transformation of the product results, solvents and impurities contained in the product being dissolved. The product is filtered, washed with 100 ml of ethanol and dried under vacuum at 50° C. 97 g of product are obtained with 3,3% moisture, purity 96,6%, containing less than 0,1% ethanol as solvent.

EXAMPLE 5

100 g of raw sodium oxacillin, obtained by concentration to dryness of crystallization mother-liquors, are dissolved in a mixture of 200 ml water and 200 ml ethanol. The solution is filtered and to the filtered solution 2000 ml of absolute ethanol are slowly added. The crystallization is continued over a period of 4 h, while cooling at 0° C.

The mixture is filtered, the filter-cake washed with 200 ml of 95% ethanol and dried under vacuum up to constant weight. 92 g of product are obtained, 3,8% moisture content, purity 96%, purity of dry product 99,8%, solvent content less than 0,2%.

EXAMPLE 6

100 g of acid cefotoxime are dissolved in 2 l of ethyl acetate. The solution is treated with 5 g of coal to remove the colour. 1000 ml of water are added and pH adjusted to 6,8 with sodium bicarbonate. The phases are separated and the aqueous phase is freeze-dried so as to obtain a dry product with a moisture content of less than 0,5%.

The resulting solid material is suspended in 800 ml of absolute ethanol at −30° C. The mixture is stirred up to complete dissolution, the solution is filtered and the filter washed with 200 ml of absolute ethanol at −30° C.

The solution is then quickly heated to +15° C., stirred for 4 h up to complete crystallization, cooled to 0° C. stirred for 2 h and the resulting product is filtered and washed with 200 ml of absolute ethanol at 0° C. 90 g of finished product are obtained, having a purity of 96%.

EXAMPLE 7

100 g of sodium cefalotin, obtained by freeze-drying, are suspended in 500 ml of absolute ethanol. The suspension is stirred for 1 h at 20° C. until the product is completely transformed. The product is filtered, washed with 100 ml of absolute ethanol and dried under vacuum at 40° C. 97 g of finished product are obtained, purity (dry product) 98%, loss to dryness less than 0,5%.

EXAMPLE 8

100 g of sodium cefazolin, obtained by freeze-drying from the corresponding acid, are dissolved in 300 ml of a water-ethanol mixture. To the filtered solution 1500 ml of absolute ethanol are added and the mixture is cooled to 0° C. and gently stirred for 4 h to get the product crystallized. The product is filtered, washed with 200 ml of absolute ethanol and dried under vacuum at 50° C. up to constant weight.

A product is obtained, 96% pure, having moisture content of 3,2%, purity of the dry product 99,2%.

EXAMPLE 9

100 g of spray-dried sodium cefuroxime are dissolved in 1500 ml of ethanol at −20° C.; the solution is filtered and slowly heated up to 20° C. The crystallization is carried out over a 2h period, the mixture is cooled to 0° C., filtered and the filter-cake washed with 300 ml of absolute ethanol.

The product is filtered under vacuum and dried up to constant weight.

A product is obtained having 2,8% moisture, purity: wet product 96,8%, dry product 99,6%, solvent content less than 0,2%.

I claim:

1. A process for producing a pure crystalline product, characterized in that a starting material comprising penicillins and cephalosporins selected from the group consisting of cloxacillin, flucloxacillin, oxacillin, cefotoxime, cefalotin, cefazolin and cefuroxime, as an acid or salt thereof, in an amorphous or in a crystalline form retaining a pharmaceutically unacceptable solvent, (1) is treated under stirring with hydrous or anhydrous ethanol at a temperature between about −30° C. and 30° C. to give an intermediate product which, in its crystalline form, is washed with absolute ethanol to replace said pharmaceutically unacceptable solvent with ethanol, and (2) the isolated crystalline intermediate product is heated at about 40° to 50° C. to substantially eliminate ethanol which, by spontaneous hydration, is replaced by water in the product crystals to yield a final product which is a pharmaceutically acceptable, stable and substantially pure crystalline form with a content of ethanol lower than 0.2%.

* * * * *